(12) United States Patent
Moenning, Jr.

(10) Patent No.: US 8,479,737 B2
(45) Date of Patent: *Jul. 9, 2013

(54) COMBINATION ANESTHESIA AND SCAVENGER SURGICAL MASK

(76) Inventor: John E. Moenning, Jr., Noblesville, IN (US)

(*) Notice: Subject to any disclaimer, the term of this patent is extended or adjusted under 35 U.S.C. 154(b) by 1001 days.

This patent is subject to a terminal disclaimer.

(21) Appl. No.: 12/540,085

(22) Filed: Aug. 12, 2009

(65) Prior Publication Data

US 2010/0122706 A1   May 20, 2010

Related U.S. Application Data

(63) Continuation of application No. 12/273,748, filed on Nov. 19, 2008, now Pat. No. 8,291,905.

(51) Int. Cl.
*A61M 16/00* (2006.01)
*A62B 18/02* (2006.01)

(52) U.S. Cl.
USPC ............ 128/206.21; 128/203.29; 128/206.28; 128/910

(58) Field of Classification Search
USPC ............. 128/203.29, 205.27, 206.21, 206.28, 128/207.13, 207.18, 910
IPC ................................ A61M 16/00; A62B 18/02
See application file for complete search history.

(56) References Cited

U.S. PATENT DOCUMENTS

| | | | |
|---|---|---|---|
| 1,044,031 A | 11/1912 | Drager | |
| 2,868,198 A | 1/1959 | Brooke | |
| 3,747,599 A | 7/1973 | Malmin | |
| 4,248,218 A | 2/1981 | Fischer | |
| 4,265,239 A | 5/1981 | Fischer, Jr. et al. | |
| 4,770,169 A | 9/1988 | Schmoegner et al. | |
| 4,794,921 A | 1/1989 | Lindkvist | |
| 4,807,617 A | 2/1989 | Nesti | |
| 4,895,172 A | 1/1990 | Lindkvist | |
| 4,945,906 A | 8/1990 | Lindkvist | |
| 4,949,714 A | 8/1990 | Orr | |
| 5,005,571 A | 4/1991 | Dietz | |
| 5,311,862 A | 5/1994 | Blasdell et al. | |
| 5,322,059 A | 6/1994 | Walther | |
| 5,370,110 A | 12/1994 | Corn | |
| 5,400,781 A | 3/1995 | Davenport | |
| 5,419,317 A | 5/1995 | Blasdell et al. | |
| 5,474,060 A | 12/1995 | Evans | |
| 5,513,632 A | 5/1996 | Nepon et al. | |
| 5,676,133 A | 10/1997 | Hickle et al. | |
| 5,715,813 A | 2/1998 | Guevrekian | |
| 5,871,011 A * | 2/1999 | Howell et al. | ............ 128/206.22 |
| 6,076,524 A | 6/2000 | Corn | |
| 6,237,596 B1 | 5/2001 | Bohmfalk | |
| 6,263,874 B1 | 7/2001 | LeDez et al. | |

(Continued)

OTHER PUBLICATIONS

International Search Report for International Patent Publication No. PCT/US2009/064713, May 6, 2010, 12 pgs.

(Continued)

*Primary Examiner* — Oren Ginsberg

(74) *Attorney, Agent, or Firm* — Barnes & Thornburg LLP

(57) ABSTRACT

A surgical mask for administering and/or scavenging medical gases includes a nasal mask and an oral mask that envelops the nasal mask. The nasal mask is secured to the oral mask and may be removable from it.

18 Claims, 5 Drawing Sheets

U.S. PATENT DOCUMENTS

| | | |
|---|---|---|
| 6,357,437 B1 | 3/2002 | Jacques |
| 6,698,427 B1 | 3/2004 | Clowers |
| 6,736,140 B1 | 5/2004 | Baczkowski |
| 7,100,611 B2 * | 9/2006 | Yu .......................... 128/206.29 |
| 7,144,498 B2 | 12/2006 | McCall et al. |
| 7,481,221 B2 | 1/2009 | Kullik et al. |
| 7,513,252 B2 | 4/2009 | Berg |
| 2006/0076013 A1 | 4/2006 | Berg |
| 2006/0174889 A1 | 8/2006 | Noble |
| 2008/0276941 A1 | 11/2008 | Doty et al. |
| 2008/0295845 A1 | 12/2008 | Nashed |
| 2010/0122704 A1 * | 5/2010 | Moenning, Jr. .......... 128/206.24 |
| 2010/0122705 A1 * | 5/2010 | Moenning, Jr. .......... 128/206.24 |

OTHER PUBLICATIONS

Summer et al., "Sevoflurane in Exhaled Air of Operating Room Personnel," 2003, 1070-1073, 97, Anesthesia & Analgesia, Austria.

Sessler et al., "Exposure of Postoperative Nurses to Exhaled Anesthetic Gases," 1998, 1083-1088, 87, Anesthesia & Analgesia.

Jiang et al., "The Principle of Upper Airway Unidirectional Flow Facilitates Breathing in Humans," 2008, 854-858, 105, Journal of Applied Physiology.

"Waste Anesthetic Gases—Occupational Hazards in Hospitals," National Institute for Occupational Safety and Health, Sep. 2007, DHHS (NIOSH) Publication No. 2007-151.

"Class II Special Controls Guidance Document: Filtering Facepiece Respirator for Use by the General Public in Public Health Medical Emergencies," Jul. 3, 2007, Center for Devices and Radiological Health—Guidance for Industry and FDA Staff.

Badgwell, J. Michael, "An Evaluation of Air Safety Source-Control Technology for the Post Anesthesia Care Unit," Journal of PeriAnesthesia Nursing, Aug. 1996, 207-222, 4.

Wharton, David F., "ASPAN's Environmental Health Task Force: Guarding the Health of Our Members," Journal of PeriAnesthesia Nursing, Aug. 1996, 202-203, 4.

"American Society of PeriAnesthesia Nurses—A Position Statement on Air Safety in the PeriAnesthesia Environment," Journal of PeriAnesthesia Nursing, Aug. 1996, 204-205, 4.

Ginsburg, William H., "Legal Issues in the Post Anesthesia Care Unit," Journal of PeriAnesthesia Nursing, Aug. 1996, 267-272, 4.

* cited by examiner

COMBINATION ANESTHESIA AND SCAVENGER SURGICAL MASK

CLAIM OF PRIORITY

This application is a continuation of U.S. patent application Ser. No. 12/273,748, now U.S. Pat. No. 8,291,905, which is entitled "Combination Anesthesia and Scavenger Mask" and was filed on Nov. 19, 2008 by John E. Moenning, Jr., the entirety of which is hereby incorporated by reference.

CROSS REFERENCE TO RELATED APPLICATION

Cross reference is also made to co-pending U.S. patent application Ser. No. 12/540,082 which is entitled "Combination Anesthesia and Scavenger Mask" and is being filed concurrently herewith by John E. Moenning, Jr., and is hereby incorporated by reference in its entirety.

TECHNICAL FIELD

The present disclosure relates generally to surgical masks, and more particularly to surgical masks used in the administration and scavenging of anesthesia gases.

BACKGROUND

Anesthesia gases are used on patients during surgical procedures. The administration of anesthesia gases to a patient involves the use of a mask placed over the nose and/or mouth of the patient. A gas administration circuit pumps the anesthesia gases into the mask for the patient to inhale through the nose and/or mouth.

SUMMARY

According to one aspect, there is provided a surgical mask having a nasal mask nested within an oral mask. Medical gases such as anesthesia gases and recovery gases are administered to a patient through the nasal mask. Gases exhaled by the patient are captured by the oral mask and exhausted to a scavenger circuit.

According to another aspect, a surgical mask assembly for administering and scavenging medical gases includes an outer mask having a first gas port configured to be coupled to a negative pressure source, and an inner mask secured to, and enveloped by, the outer mask. The inner mask has a second gas port that is configured to be coupled to a positive pressure source.

The outer mask may include a shell which defines a chamber with a rear-facing opening defined by a rim, along with a flexible seal secured to the rim.

The inner mask may be located in the chamber of the shell of the outer mask.

The inner mask may include a shell which defines a chamber with a rear-facing opening defined by a rim, and along with a flexible seal secured to the rim. The shell of the inner mask may be located in the chamber of the shell of the outer mask. In some embodiments, both the shell and the flexible seal of the inner mask may be located in the chamber of the shell of the outer mask.

The flexible seal of the inner mask seals the chamber of the inner mask from the chamber of the outer mask when the surgical mask assembly is positioned on the face of a patient.

The flexible seal of the outer mask envelops a patient's nose and mouth when the surgical mask assembly is positioned on the face of the patient, whereas the flexible seal of the inner mask envelops the patient's nose when the surgical mask assembly is positioned on the face of the patient.

The inner mask may be removable from the outer mask. In such embodiments, the outer mask may have an aperture defined therein, with the inner mask having a hollow tube extending outwardly therefrom. The hollow tube may be press fit into the aperture. The hollow tube may open into the chamber of the inner mask.

According to another aspect, a surgical mask assembly for administering and scavenging medical gases includes an oral mask and a nasal mask. The oral mask has a shell which defines a chamber with a rear-facing opening defined by a rim, a flexible seal secured to the rim, and a gas port. The flexible seal of the oral mask envelops a patient's nose and mouth when the surgical mask assembly is positioned on the face of the patient. The nasal mask includes a shell which defines a chamber with a rear-facing opening defined by a rim, a flexible seal secured to the rim, and a gas port. The flexible seal of the nasal mask envelops the patient's nose when the surgical mask assembly is positioned on the face of the patient.

The nasal mask may be located in the chamber of the shell of the oral mask.

The shell of the nasal mask may be located in the chamber of the shell of the oral mask. In some embodiments, both the shell and the flexible seal of the nasal mask are located in the chamber of the shell of the oral mask.

The flexible seal of the nasal mask seals the chamber of the nasal mask from the chamber of the oral mask when the surgical mask assembly is positioned on the face of a patient.

The nasal mask may be removable from the oral mask. In such embodiments, the shell of the oral mask may have an aperture defined therein, with the nasal mask having a hollow tube extending outwardly from the shell nasal mask. The hollow tube may open into the chamber of the nasal mask. The hollow tube may be press fit into the aperture defined in the shell of the oral mask.

According to another aspect, a method of administering medical gases to a patient during and subsequent to a medical procedure includes first coupling an oral mask to a source of anesthesia gas and supplying anesthesia gas to the patient via the oral mask. Then the oral mask may be decoupled from the source of anesthesia gas and coupled to a negative pressure source. A nasal mask may then be secured to the oral mask. The nasal mask is coupled to a source of post-operative recovery gas. The post-operative gas is supplied to the patient via the nasal mask and gas exhaled by the patient is evacuated via the oral mask.

The oral mask may be secured to the source of anesthesia gas during the medical procedure, and decoupled from source of anesthesia gas at completion of the medical procedure. The oral mask is coupled to the negative pressure source at completion of the medical procedure.

The post-operative recovery gas may be oxygen with such oxygen being supplied to the nasal mask to be inhaled through the patient's nose. The gases exhaled by the patient are evacuated via the oral mask.

BRIEF DESCRIPTION OF THE DRAWINGS

The detailed description particularly refers to the following figures, in which.

DETAILED DESCRIPTION OF THE DRAWINGS

Figure 1:
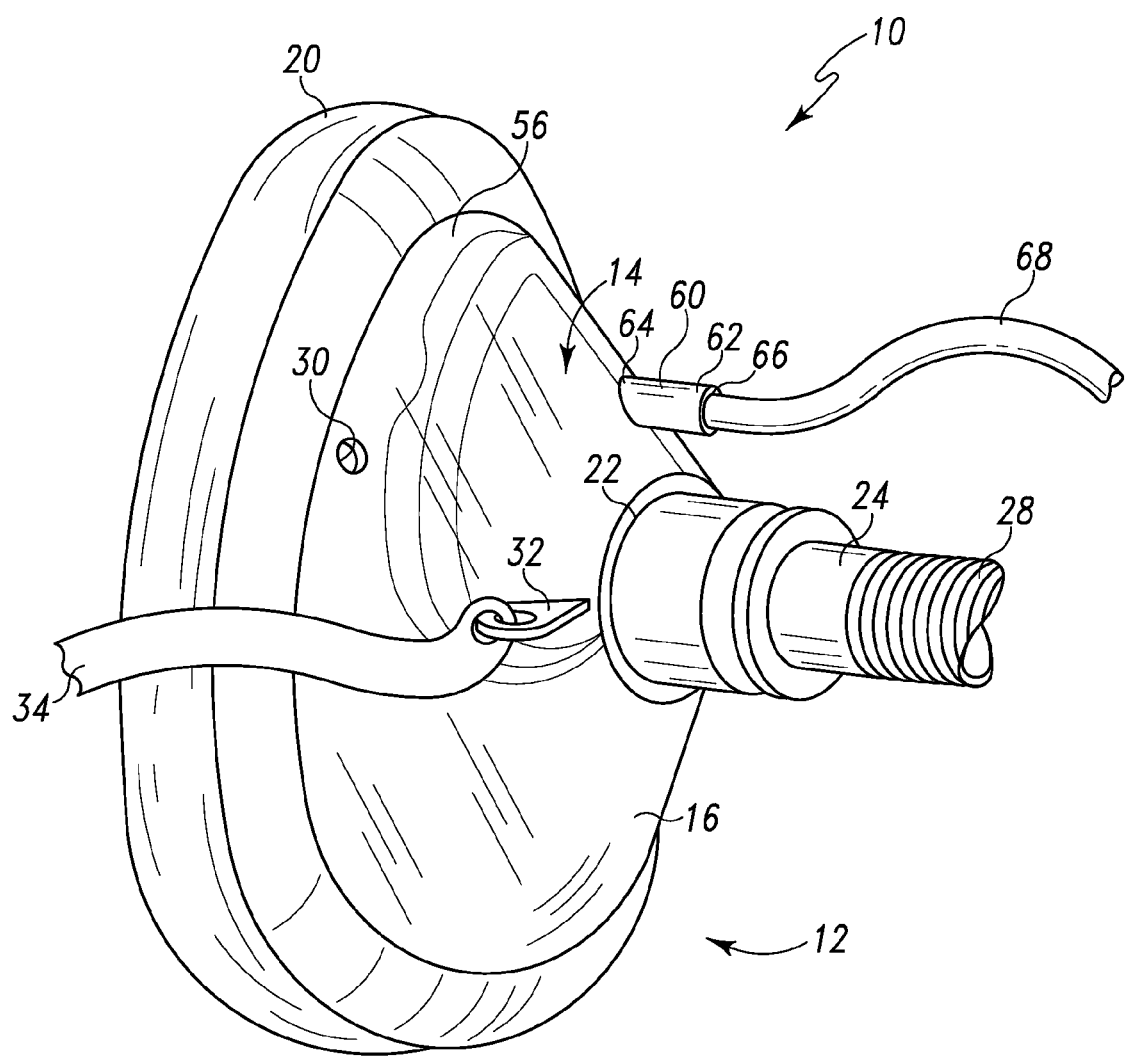
FIG. 1 is a perspective view of one embodiment of a surgical mask.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Figure 2:
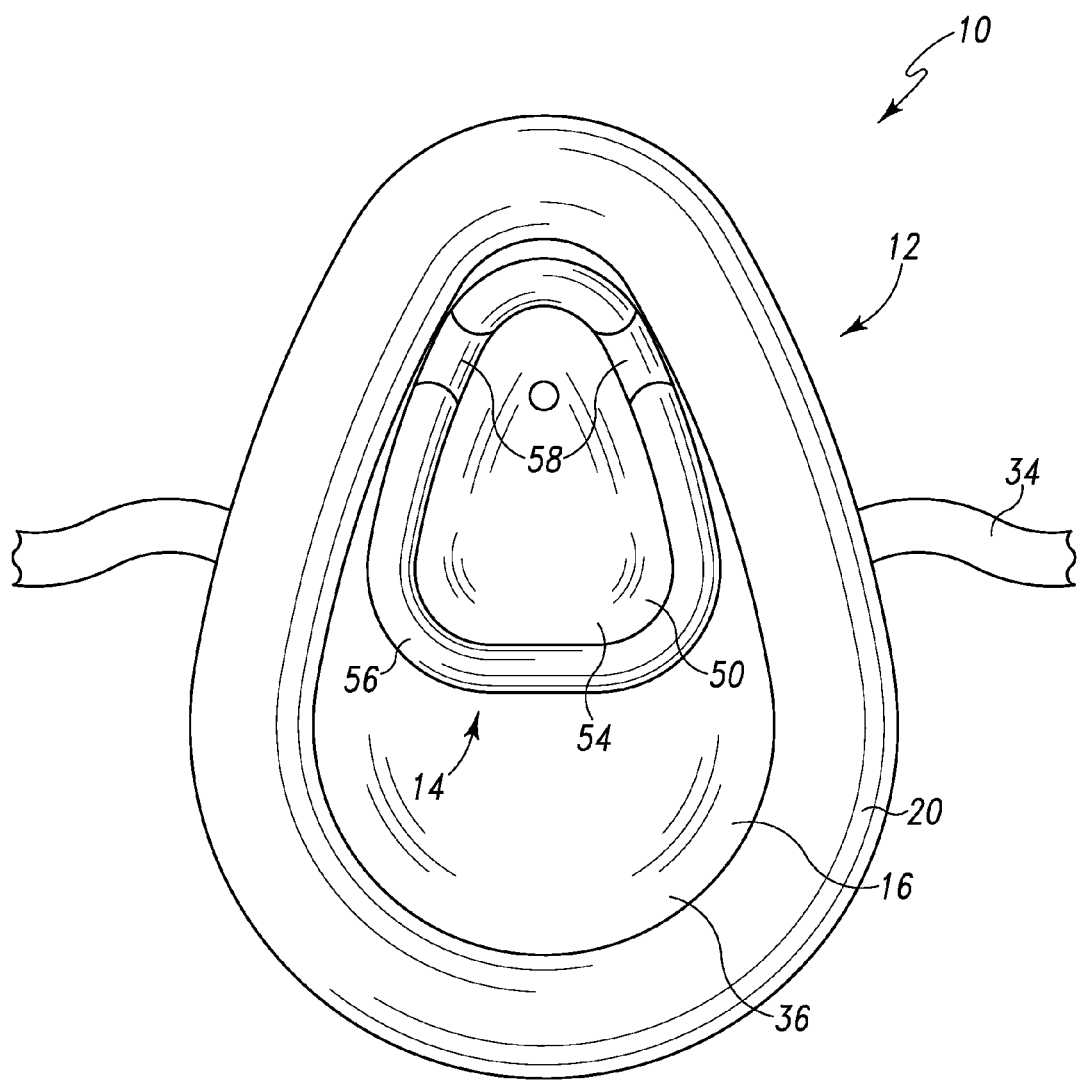
FIG. 2 is rear elevation view of the surgical mask of FIG. 1.
Figure 3:
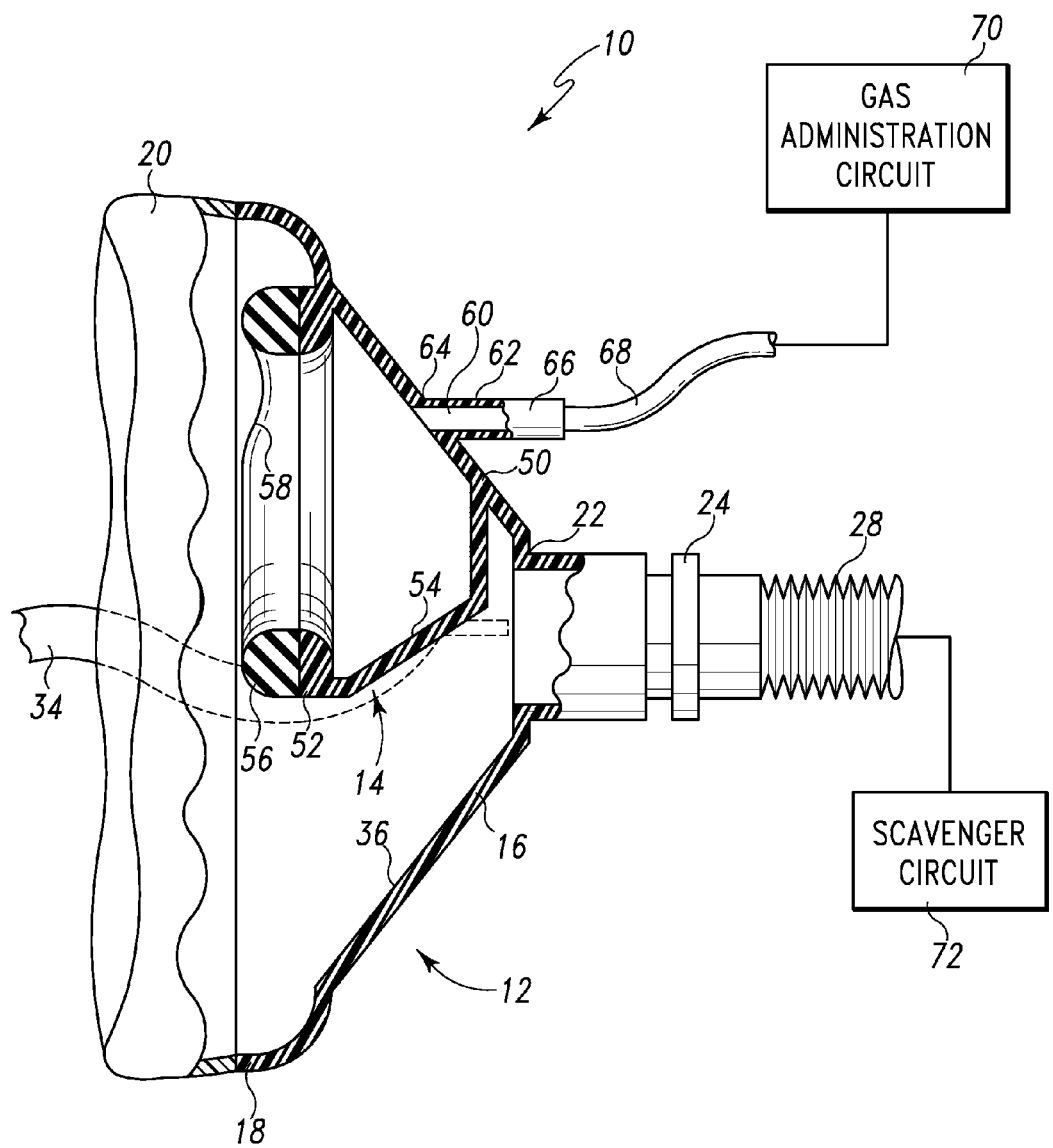
FIG. 3 is a cross-sectional view of the surgical mask of FIG. 1.

Referring to FIGS. 1-3, there is shown an illustrative embodiment of a combined anesthesia and scavenger surgical mask assembly 10 (hereinafter, simply, "surgical mask 10"). As will be discussed herein in greater detail, the surgical mask 10 may be used to deliver anesthesia or other medical gases to be inhaled by a patient. The surgical mask 10 also functions to scavenge the gases exhaled by the patient.

In the illustrative embodiment described herein, the surgical mask 10 includes an oral mask 12 having a nasal mask 14 nested therein. The oral mask 12 includes rigid or semi-rigid plastic shell 16. As best seen in FIG. 3, the shell 16 defines a hollow chamber 36 having a rear-facing opening defined by a rim 18. As can be seen in FIG. 2, the rear-facing opening of the shell 16 is generally pear-shaped when viewed from the rear of the mask. A pillow-type seal 20 is secured to the rim 18 of the shell 16. In the illustrative embodiment described herein, the seal 20 is embodied as a soft, flexible, air-filled bladder, although other types of seals may also be used. The seal 20 deforms to correspond with the contour of a patient's face when the doctor places the surgical mask 10 over the patient's nose and mouth. When the surgical mask 10 is positioned on the patient's face, the seal 20 envelops the area around the patient's nose and mouth in such a way as to create a seal between the oral mask 12 and the patient's face. In such a way, the patient's nose and mouth are sealed within the chamber 36.

A gas port 22 is defined in the shell 16 of the oral mask 12. The gas port 22 includes a hollow tube 24 that extends outwardly from the oral chamber 36. The hollow tube 24 has a proximal end that opens into the oral chamber 36. A threaded distal end 28 of the hollow tube 24 may be coupled (e.g., screwed) to a hose or other type of fluid line of a scavenger circuit 72 (see FIG. 3). As such, the chamber 36 of the oral mask 12 may be exposed to the negative fluid pressure generated by the scavenger circuit 72. In other words, when the threaded distal end 28 of the hollow tube 24 is coupled to the scavenger circuit 72, a vacuum pump (not shown) associated with the scavenger circuit 72 may be used to evacuate the gases exhaled by the patient into the oral mask 12. Although the distal end 28 of the hollow tube 24 is herein described as being threaded, it should be appreciated that other configurations may also be used to couple the oral mask 12 to the scavenger circuit.

The oral mask 12 also includes a number of holes 30 extending through the shell 16. The holes 30 allow for minor venting of the chamber 36 of the oral mask 12 when it is subjected to negative fluid pressure from the scavenger circuit 72. This prevents the oral mask 12 from uncomfortably locking onto the patient's face due to the suction generated by the scavenger circuit 72. The negative pressure in the chamber 36 of the oral mask 12 prevents exhaled gases from escaping through the holes 30.

One of a pair of strap mounts 32 is formed in the shell 16 of the oral mask 16 on either side of the port 22. An elastic strap 34 is secured to the strap mounts 32 and may be used to secure the surgical mask 10 to the patient's head.

As shown best in the cross section of FIG. 3, the oral mask 12 envelops the nasal mask 14. More specifically, the nasal mask 14 is located within the chamber 36 such that the chamber 36 envelops the nasal mask 14. When the surgical mask 10 is placed over the patient's face, the seal 20 also functions to seal the nasal mask 14 within the chamber 36.

Like the oral mask 12, the nasal mask 14 includes rigid or semi-rigid plastic shell 50. As best seen in FIG. 3, the shell 50 defines a hollow chamber 54 having a rear-facing opening defined by a rim 52. As can be seen in FIG. 2, the rear-facing opening of the shell 50 is generally pear-shaped when viewed from the rear of the mask. A flexible seal 56 is secured to the rim 52 of the shell 50. In the illustrative embodiment described herein, the seal 56 is embodied as a soft, flexible sealing ring, although other types of seals may also be used. The seal 56 corresponds with the contour of a patient's nose and the area of the face surrounding the nose when the doctor places the surgical mask 10 over the patient's nose and mouth.

A gas port 60 is defined in the shell 50 of the nasal mask 14. Although only one gas port 60 is shown in the illustrative embodiment described herein, it should be appreciated that any number of gas ports may be used. Moreover, the gas port 60 (or ports) may be located at various locations in the shell 50 to fit the needs of a given design. The gas port 60 includes a hollow tube 62 that extends outwardly from the nasal chamber 54. The hollow tube 62 has a proximal end 64 that opens into the nasal chamber 54. A distal end 66 of the hollow tube 62 may be coupled to a hose 68 or other type of fluid line of a medical gas administration circuit 70 (see FIG. 3). As such, the chamber 54 of the nasal mask 14 may be exposed to the medical gases (e.g., anesthesia gases or oxygen) supplied by the gas administration circuit 72. In other words, when the distal end 66 of the hollow tube 62 is coupled to the gas administration circuit 70, a supply pump (not shown) or pressurized tank (not shown) associated with the gas administration circuit 70 may be used to supply medical gases under positive pressure to the chamber 54 of the nasal mask 14 where such gases are then inhaled by the patient through the patient's nose. Although the distal end 66 of the hollow tube 62 is herein described as being slip fit onto the hose of the gas administration circuit 70, it should be appreciated that other configurations may also be used to couple the nasal mask 14 to the gas administration circuit.

The flexible seal 56 of the nasal mask 14 seals the chamber 54 of the nasal mask from the chamber 36 of the oral mask 12. In particular, when the surgical mask 10 is placed on the face of a patient, the flexible seal 56 seals to the patient's nose and the area of the face surrounding the nose thereby fluidly isolating the chamber 54 of the nasal mask from the chamber 36 of the oral mask 12. In such a way, medical gases (e.g., anesthesia gases or recovery oxygen) supplied by the gas administration circuit 72 can accumulate within the chamber 54 of the nasal mask 14 to be inhaled by the patient without being evacuated by the scavenger circuit 72 through the oral mask 12.

As shown in FIGS. 2 and 3, a pair of curved indentations 58 are formed in the rear edge of the flexible seal 56 near the portion of the seal 56 that engages the bridge of the patient's nose. The curved indentations 58 provide for a minor amount of selective fluid communication between the chamber 54 of the nasal mask 14 and the chamber 36 of the oral mask 12. Specifically, if the patient exhales heavily through his or her nostrils, the nasal mask is gently urged away from the bridge of the patient's nose. This allows the exhaled gases exiting through the patient's nostrils to pass from the chamber 54 of the nasal mask 14 into the chamber 36 of the oral mask 12 through the opening created by the space between the curved indentations 58 and the patient's nose.

In use, the surgical mask 10 may be positioned over the patient's nose and mouth to administer medical gases such as anesthesia gases to the patient. The strap 34 secures the mask 10 to the patient's head. The hollow tube 62 of the mask's gas port 60 is coupled to the hose 68 of the gas administration circuit 70. The hollow tube 24 of the gas port 22 is coupled to the hose of the scavenger circuit 72.

Once coupled in such a manner and strapped to the patient, anesthesia gases from the gas administration circuit 70 are allowed to flow into the chamber 54 of the nasal mask 14 via the mask's gas port 60. The patient inhales the anesthesia gases that accumulate in the chamber 54 through the nose. Meanwhile, the scavenger circuit 72 creates negative pressure in the chamber 36 of the oral mask 12. This negative pressure pulls gases exhaled from the patient's mouth out of the surgical mask 10 and into the scavenger circuit where they are processed and disposed.

The holes 30 formed in the shell of the oral mask 12 prevent the oral mask 12 from locking onto the patient's face due to the suction created by the negative pressure. Moreover, to the extent the patient exhales heavily out of his or her nostrils, the curved indentations 58 of the nasal mask 14 provide a fluid path that allows the exhaled gases from the patient's nostrils to pass from the nasal chamber 54 into the oral chamber 36 where they are scavenged along with the gases exhaled from the patient's mouth.

During post-operative recovery, the gas administration circuit 70 (or other gas source) may be operated to supply recovery gas, such as oxygen, to the patient via the hollow tube 62 of the mask's gas port 60. During such post-operative recovery, the patient will continue to outgas the anesthesia gases administered to the patient during the surgical procedure. As such, the scavenger circuit 72 continues to create negative pressure in the chamber 36 of the oral mask 12 thereby allowing the exhaled gases from the patient's mouth to be pulled from the surgical mask 10 during post-operative recovery.

Figure 4:
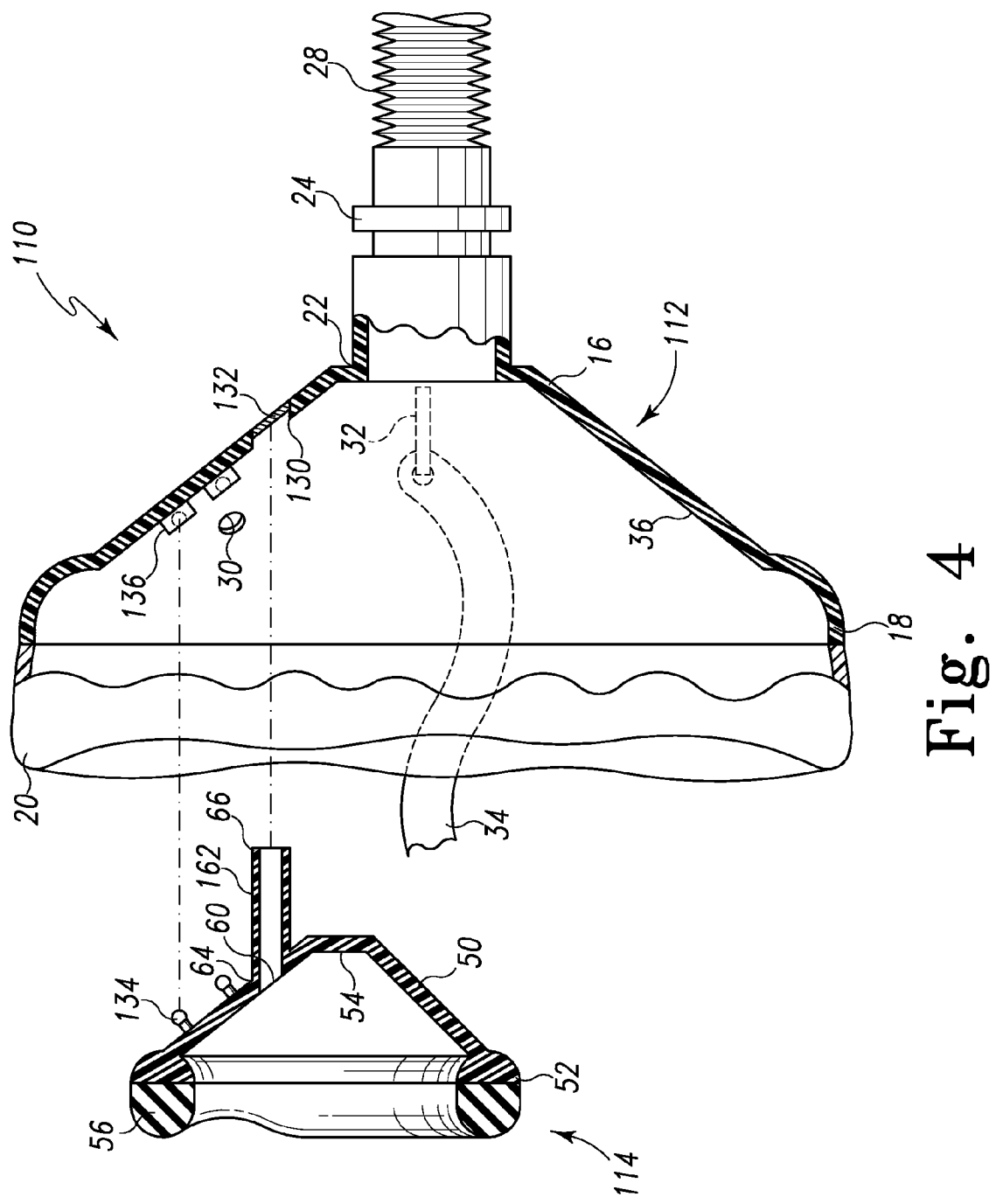
FIG. 4 is a cross-sectional view of another embodiment of a surgical mask.
Figure 5:
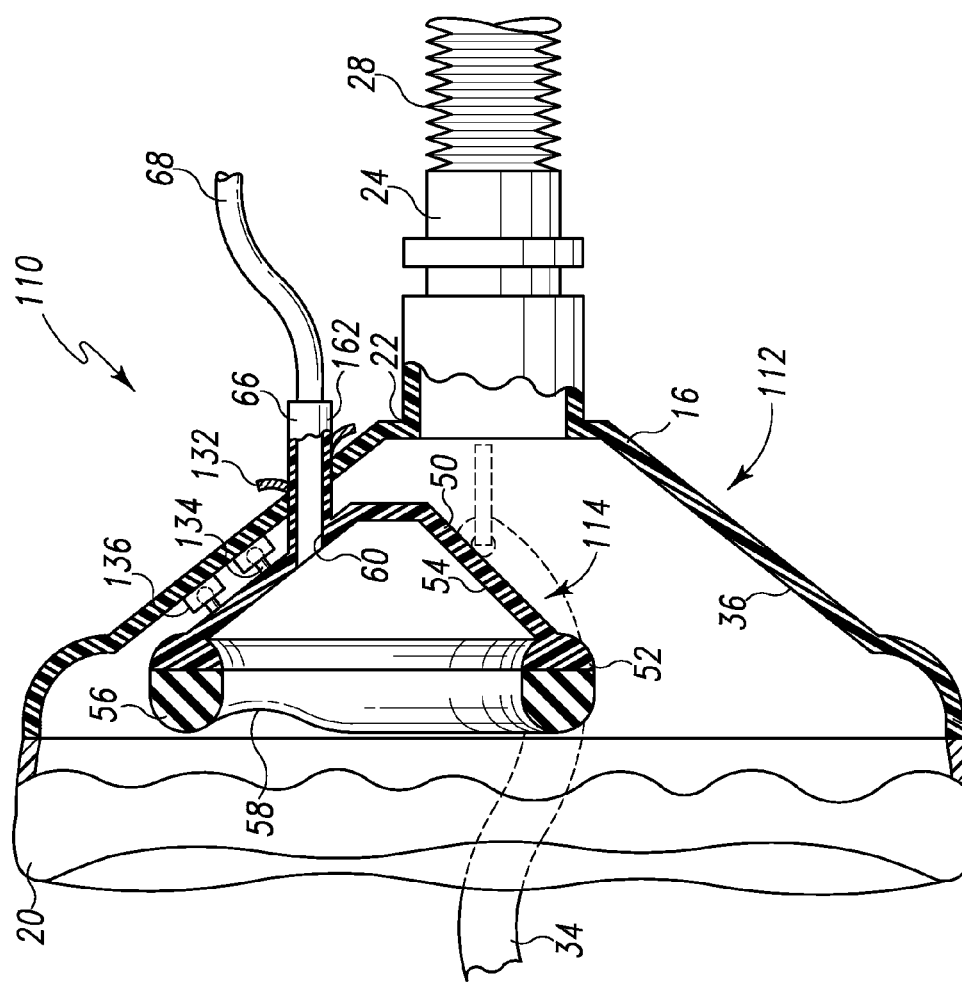
FIG. 5 is another cross-sectional view of the surgical mask of FIG. 4.

Referring now to FIGS. 4 and 5, a different embodiment of a surgical mask is shown (hereinafter referenced as a surgical mask 110). Some features of the embodiment illustrated in FIGS. 4 and 5 are substantially similar to those discussed above in reference to the embodiment of FIGS. 1-3. Such features are designated in FIGS. 4 and 5 with the same reference numbers as those used in FIGS. 1-3.

In the case of the surgical mask 110, the nasal mask 114 is removable from the oral mask 112. In such an arrangement, the oral mask 112 may be used as a conventional anesthesia mask when the nasal mask 114 is not attached. That is, the gas administration circuit 70 may be connected to the surgical mask 110 via the threaded distal end 28 of the oral mask 112. In this way, anesthesia gases may be delivered into the chamber 36 of the oral mask 112 where they are inhaled by the patient through the nose and/or the mouth.

The plastic shell 16 of the oral mask 112 has an aperture 130 formed therein. A cover 132 seals the aperture 130 thereby preventing gases within the chamber 36 from escaping through the aperture 130. The cover 132 may be made of a foil or plastic that can be torn, ripped, or pulled free from the oral mask 112. It should be appreciated that in other embodiments the cover 132 may be made of rubber or other suitable material.

A tapered hollow tube 162 extends outwardly from the nasal chamber 54 of the nasal mask 114. The hollow tube 162 has a proximal end 64 that opens into the nasal chamber 54. The distal end 66 of the hollow tube 162 may be coupled to the hose 68 or other type of fluid line of a medical gas administration circuit 70 (see FIG. 3). The outer diameter of the tapered hollow tube 162 increases from its distal end 66 in the direction toward its proximal end 64. Such an arrangement allows the tapered hollow tube 162 to be press fit (i.e., friction fit) into the aperture 130 formed in the plastic shell 16 of the oral mask 112 (see FIG. 5) thereby securing the nasal mask 114 to the oral mask 112.

The outer surface of the shell 50 of nasal mask 114 has a number of snap pins 134 extending outwardly therefrom. The inner surface of the shell 16 of the oral mask 112 has a corresponding number of catches or clips 136. The clips 136 of the oral mask 112 receive the snap pins 134 of the nasal mask 114 thereby securing the nasal mask 114 to the oral mask 112, as illustrated in FIG. 5. It should be appreciated that in other embodiments, other fasteners, joints, etc. may be used to secure the nasal mask 114 to the oral mask 112.

In use, the oral mask 112 may be used without the nasal mask 114 as a conventional anesthesia mask during surgery. In such an arrangement, the hollow tube 24 of the gas port 22 is coupled to a source of anesthesia gas (e.g., the gas administration circuit 70) so that anesthesia gases may flow into the chamber 36 of the oral mask 112 where they are inhaled by the patient through the nose and mouth. At the end of surgery, the oral mask 112 may then be converted to a scavenger mask for use in post-operative recovery in a similar manner to as described above in regard to the surgical mask 10. In particular, during post-operative recovery, the oral mask 112 may be disconnected from the gas administration circuit 70 (or other source of anesthesia gas) and connected to the scavenger circuit 72 by coupling the threaded distal end 28 of the hollow tube 24 to the scavenger circuit.

During such conversion of the oral mask 112, the nasal mask 114 may be installed to provide recovery gas (e.g., oxygen) to the patient. In particular, the nasal mask 114 may be advanced into the chamber 36 of the oral mask 112 so that the distal end 66 of its tapered hollow tube 162 is aligned with the aperture 130 formed in the plastic shell 16 of the oral mask 112. The distal end 66 of the hollow tube 162 is then urged into contact with the cover 132 thereby puncturing the cover 132. The hollow tube 162 is then press fit (i.e., friction fit) into the aperture 130 formed in the plastic shell 16 of the oral mask 112 (see FIG. 5). During such advancement of the nasal mask 114, the clips 136 of the oral mask 112 receive the snap pins 134 of the nasal mask 114. The combination of the press-fit connection of the tapered hollow tube 162 and the snap pins 134 secures the nasal mask 114 to the oral mask 112.

Once the nasal mask 114 is secured to the oral mask 112, it is connected to the gas administration circuit 70 via the tapered hollow tube 162. In such a way, the surgical mask 110 then functions similarly to the surgical mask 10 of FIGS. 1-3. In particular, during post-operative recovery, the gas administration circuit 70 (or other gas source) may be operated to supply recovery gas, such as oxygen, to the patient via the hollow tube 162 of the mask's gas port 60. During such post-operative recovery, the patient will continue to outgas the anesthesia gases administered to the patient during the surgical procedure. As such, the scavenger circuit 72 continues to create negative pressure in the chamber 36 of the oral mask 112 thereby allowing the exhaled gases from the patient's mouth to be pulled from the surgical mask 110 during post-operative recovery.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A surgical mask assembly for administering and scavenging medical gases, comprising:
    an outer shell having a first gas port configured to be coupled to a negative pressure source, the outer shell defining a chamber with a rear-facing opening defined by a rim, and
    an inner shell secured to the outer shell, the inner shell defining a chamber with a rear-facing opening defined by a rim and having a second gas port that includes (i) a distal end configured to be coupled to a positive pressure source, and (ii) a proximal end that opens into the chamber of the inner shell such that gas from the positive pressure source is advanced through second gas port and out of the chamber of the inner shell to exit the inner shell, wherein the rim of the inner shell is enveloped by the outer shell.

2. The surgical mask assembly of claim 1, wherein: the inner shell is located in the chamber of the outer shell.

3. The surgical mask assembly of claim 1, wherein: a flexible seal secured to the rim of the inner shell, and the flexible seal is located in the chamber of the outer shell.

4. The surgical mask assembly of claim 1, wherein: the rim of the inner shell is located in the chamber of the outer shell.

5. The surgical mask assembly of claim 1, wherein: the outer shell envelops a patient's nose and mouth when the surgical mask assembly is positioned on the face of the patient, and
    the inner shell envelops the patient's nose when the surgical mask assembly is positioned on the face of the patient.

6. The surgical mask assembly of claim 1, wherein: a flexible seal is secured to the rim of the inner shell.

7. The surgical mask assembly of claim 6, wherein: a flexible seal is secured to the rim of the outer shell.

8. A surgical mask assembly for administering and scavenging medical gases, comprising:
    an oral mask having (i) a shell which defines a chamber with a rear-facing opening defined by a rim, and (ii) a gas port, wherein the rim of the shell of the oral mask envelops a patient's nose and mouth when the surgical mask assembly is positioned on the face of the patient, and
    a nasal mask having (i) a shell which defines a chamber with a rear-facing opening defined by a rim, and (ii) a gas port, wherein the rim of the shell of the nasal mask (a) is enveloped by the shell of the oral mask, and (b) envelops the patient's nose when the surgical mask assembly is positioned on the face of the patient.

9. The surgical mask assembly of claim 8, wherein the nasal mask is located in the chamber of the shell of the oral mask.

10. The surgical mask assembly of claim 8, wherein both the shell and the rim of the nasal mask are located in the chamber of the shell of the oral mask.

11. The surgical mask assembly of claim 8, wherein:
    a flexible seal is secured to the rim of the shell of the nasal mask, and
    both the shell and the flexible seal of the nasal mask are located in the chamber of the shell of the oral mask.

12. The surgical mask assembly of claim 8, wherein the shell of the nasal mask is located in the chamber of the shell of the oral mask.

13. A surgical mask assembly for administering and scavenging medical gases, comprising:
    an oral mask having (i) a shell which defines a chamber with a rear-facing opening defined by a rim, and (ii) a gas port, wherein the rim of the shell of the oral mask envelops a patient's nose and mouth when the surgical mask assembly is positioned on the face of the patient, and
    a nasal mask having (i) a shell which defines a chamber with a rear-facing opening defined by a rim, and (ii) a gas port, wherein (a) the rim of the shell of the nasal mask envelops the patient's nose when the surgical mask assembly is positioned on the face of the patient, and (b) a superior-most edge of the shell of the nasal mask is positioned below a superior-most edge of the shell of the oral mask, and (c) an inferior-most edge of the shell of the nasal mask is positioned above an inferior-most edge of the shell of the oral mask.

14. The surgical mask assembly of claim 13, wherein the rim of the shell of the nasal mask is positioned in the chamber of the shell of the oral mask at a location between the rim of the shell of the oral mask and the gas port of the oral mask.

15. The surgical mask assembly of claim 13, wherein the nasal mask is located in the chamber of the shell of the oral mask.

16. The surgical mask assembly of claim 13, wherein both the shell and the rim of the nasal mask are located in the chamber of the shell of the oral mask.

17. The surgical mask assembly of claim 13, wherein:
    a flexible seal is secured to the rim of the shell of the nasal mask, and
    both the shell and the flexible seal of the nasal mask are located in the chamber of the shell of the oral mask.

18. The surgical mask assembly of claim 13, wherein the shell of the nasal mask is located in the chamber of the shell of the oral mask.

* * * * *